United States Patent [19]

Nakamura et al.

[11] Patent Number: 5,914,227
[45] Date of Patent: Jun. 22, 1999

[54] METHOD FOR EXAMINATION OF HORMONE-DEPENDENT TUMORS

[76] Inventors: Junji Nakamura, Nishiura Haitsu 2-4, 578-15, Ishibashi, Ishibachimachi, Shimotsugagun, Tochigi 329-05, Japan; Makoto Yoshihama, 1400-8, Esojimamachi, Utsunomiya-shi, Tochigi 321-01, Japan

[21] Appl. No.: 08/892,291

[22] Filed: Jul. 14, 1997

Related U.S. Application Data

[63] Continuation-in-part of application No. 08/500,878, filed as application No. PCT/JP94/00779, May 13, 1994, abandoned.

[30] Foreign Application Priority Data

Dec. 3, 1993 [JP] Japan .................................... 5-339608

[51] Int. Cl.⁶ .............................. C12Q 1/00; C12Q 1/02
[52] U.S. Cl. ................................. 435/4; 435/29; 435/375
[58] Field of Search .................................. 435/29, 4, 375

[56] References Cited

FOREIGN PATENT DOCUMENTS 0 250 262 A1   12/1987   European Pat. Off. .
02 067 296     3/1990    Japan .

OTHER PUBLICATIONS

Tuttle et al., "Effect of 5–alpha–reductase inhibition and dexamethasone administration of the growth characteristics and intratumor androgen levels of the human prostate cancer cell line PC–3" The Prostate 24 : 229–36 (1994).

T. Utsumi, "Local Production of Estrogen Via Aromatase and Estrone Sulfatase in Breast Tissue" *J. of Japan Surg. Soc.* 90(6):919–927 (1987) (English abstract).

T. Yamamoto, et al., "Estrogen Productivity of Endometrium and Endometrial Cancer Tissue; Influence of Aromatase on Proliferation of Endometrial Cancer Cells." *J. Steroid Biochem. Molec. Biol.* 44(4–6): 463–468 (1993).

The Merck Index, S. Budavari (ed.). #4899 "Invertase" pp. 792–793 (1989).

S. Abraham et al., Lipid Metabolism and Enzyme Activities in Hormone–Dependent and Hormone Independent Mammary Adenocarcinoma in GR Mice*JNCI* 77(1):233–239 (1986).

J.L. Daechnfeldt et al., "High Affinity Oestradiol Receptors and the Activity of Glucose–6–Phosphate Dehydrogenase and Lactose Synthetase in Mammary Carcinoma of Post-menopausal Women"*Br. J. Cancer 31*424–428 (1975).

K. Fukuma et al., "Hormone Dependency of Carcinoma of the Human Endometrium" *Cancer 51*288–294 (1983).

Fukuoka, M., "Antitumor Effects of Aromatase Inhibitors on the Growth of Estrogen Dependent Tumors" *Kyoto–furitsu Ika Daigaku Zasshi 101*(3):317–333 (1992).

M.D.W.G. Krekels, et al., "Aromatase in the Human Choriocarcimoma JEG–3: Inhibition by R 76 713 in Cultured Cells and in Rumors Grown in Nude Mice" *J. Steroid Biochem. Molec. Biol.* 38(4):415–422 (1991).

P.E. Lønning et al., "Treatment of Breast Cancer with Aromatese Inhibitors—Current Status and Future Prospects" *Br. J. Cancer 60*: 5–8 (1989).

Y. Osawa et al., "Multiple Functions of Aromatase and the Active Site Structure; Aromatase Its the Placental Estrogen 2–Hydroxylase" *J. Steroid Biochem. Molec. Biol.* 44(4–6):469–480 (1993).

Pizzini, A. et al., "Aromatase fails to mediate the proliferative effects of adrenal androgens on cultured MCF–7 breast cancer cells," *Int. J. Oncol 1* (6):709–712 (1992) (Abstract).

R.J. Santen et al., "Enzymatic Control of Estrogen Production in Human Breast Cancer: Relative Significance of Aromatase Versus Sulfatase Pathways" *Ann. New York Acad. of Sci. 464*:126–137 (1986).

*Primary Examiner*—Sandra E. Saucier
*Attorney, Agent, or Firm*—Testa, Hurwitz & Thibeault, LLP

[57] ABSTRACT

The invention relates to an examination method of hormone-dependent tissue, more particularly to a method for examining hormone-dependent tumors by culturing a tumor tissue in (a) a control culture medium, (b) a culture medium containing a hormone synthetase substrate, and (c) a culture medium containing a hormone synthetase substrate and a hormone synthetase inhibitor, and determining the relative growth ratios of tumor cells of (b) to (a), and (c) to (a) for diagnosing a tumor as being hormone dependent.

This invention provides a method for the simultaneous and easy determination of hormone dependent tumors and the presence of hormone synthetic enzymes. Further, this invention provides a new classification system for tumors and means for indicating medical treatment for a cancer patient.

8 Claims, No Drawings

METHOD FOR EXAMINATION OF HORMONE-DEPENDENT TUMORS

This application is a continuation-in-part of U.S. Ser. No. 08/500,878, filed May 13, 1994, now abandoned, which is a national stage of PCT/JP94/00779 filed May 13, 1994 the entire disclosure of which is incorporated herein by reference.

FIELD OF THE INVENTION

This invention relates to a method for examining tumor tissues. More specifically, the invention provides a method for the simultaneous diagnosis of the presence or absence of (a) hormone-dependent proliferation, and (b) a hormone synthetase in tissues and tumors. In particular, the invention provides methods for the diagnosis and treatment of hormone-dependent tumors and diseases.

BACKGROUND OF THE INVENTION

There is a class of tumors called "hormone-dependent" tumors, which generally occur in the target organs of hormones, and their growth can be promoted by or dependent on the presence of those hormones. For example, the growth of some mammary cancers is promoted by estrogen, the growth of some prostate cancers is promoted by androgen, and the growth of some thyroid cancers is promoted by thyroid stimulating hormone (TSH). Hormonal endocrine therapies are widely used for the treatment of such hormone-dependent tumors. For example, excision of estrogen-producing ovaries has been employed as an endocrine therapy for some estrogen-dependent mammary cancers. In addition, a widely used treatment for mammary cancer is the administration of an anti-estrogenic agent such as tamoxifen, which competes with estrogen for binding to the estrogen receptor, thereby exerting an antitumor effect. A biopsy of a mammary cancer is generally examined for the presence or absence of estrogen receptors in the cancerous tissue, in order to determine whether administration of an anti-estrogenic agent is indicated. In practice, a correlation between the presence of estrogen receptors and the clinical effectiveness of the anti-estrogenic agent is clinically significant. However, a positive estrogen receptor test can be misleading if the estrogen receptor is physiologically and functionally inactive. Tumors having estrogen receptors therefore do not necessarily exhibit estrogen-dependent proliferation.

Recent studies show that some tumors and other diseased tissues are capable of producing hormones which cause them to proliferate or cause the diseased tissue to be further aggravated. For example, some mammary cancers produce an enzyme called aromatase which converts androgens, such as testosterone, into estrogen. High estrogen levels in such cancer tissues have been reported. Uchimi et al., 90 J. JPN. SURG. SOC. 920–927(1989). An effective treatment for a tumor having aromatase activity and exhibiting estrogen-dependent proliferation is to administer an aromatase inhibitor. However, aromatase activity tests are rarely carried out on tumor tissue because of the difficulty in sampling the diseased tissue and in obtaining an adequate amount of tissue for determining enzymatic activity. Tumors are therefore usually only screened for the presence of estrogen receptors as an indication for aromatase inhibitor therapy. However, this test does not confirm the presence of aromatase activity, and may result in misdiagnosis because not all tumors having estrogen receptors exhibit aromatase activity, nor do all tumors having estrogen receptors necessarily exhibit estrogen-dependent proliferation. These problems are not only encountered in estrogen-related cancers, but also in other hormone-dependent cancers and diseases, and may involve one or more hormones.

SUMMARY OF THE INVENTION

The present invention provides a convenient method for the simultaneous determination of the presence or absence of a hormone synthetase and hormone-dependent proliferation in tumor cells. The method comprises culturing a tissue sample in a substrate for the hormone synthetase and comparing the growth of the tissue cells to growth in a control medium or in a medium containing the hormone synthetase substrate and an inhibitor for the hormone synthetase. The method thereby provides a classification system for tumors suspected of exhibiting hormone dependent growth and/or hormone synthetase activity. The invention further provides a method for diagnosing tumors and indicating the appropriateness of hormone synthetase inhibitor therapy.

DETAILED DESCRIPTION OF THE INVENTION

An important object of the present invention is to provide a method for the simultaneous diagnosis of hormone-dependent growth of tumor tissue and the presence of a hormone synthetase in the tissue. Another object of the invention is to provide an easy method for distinguishing a tumor type which has a hormone synthetase and proliferates hormone-dependantly (Type 1 from Table 1, below) from tumor types that do not contain hormone synthetases and/or are not hormone-dependent (Types 2, 3 and 4 from Table 1, below). Further, tumors can be classified into hormone-dependent proliferation types 1 and 2, and non-dependent proliferation types 3 and 4 as shown in Table 1.

TABLE 1

| Tumor Type | Hormone synthetase | Hormone dependent proliferation |
|---|---|---|
| 1 | + | + |
| 2 | − | + |
| 3 | + | − |
| 4 | − | − |

The examination method of the present invention comprises the following steps:

(1) Preparing a test sample by excision or biopsy of a tissue;

(2) Culturing portions of the tissue sample for 1–14 days in each of three different media—(a) a control medium, (b) a medium containing a hormone synthetase substrate, and (c) a medium containing a hormone synthetase substrate and an inhibitor of the hormone synthetase;

(3) Measuring the proliferation of the tissue sample cells in each of the three media; and (4) Determining the relative proliferation of the tumor cells. Tumor proliferation is determined by comparing (i) the growth of the tumor cells in the medium containing a hormone synthetase substrate (medium b) to the growth of the tumor cells in the control medium (medium a); and (ii) the growth of tumor cells in the medium containing a hormone synthetase substrate and an inhibitor for the hormone synthetase (medium c) to the growth of the tumor cells in the control medium (medium a). Thus, hormone-dependent growth of tumor tissue and the presence of a hormone synthetase can be determined simultaneously.

Tissue samples may be collected, for example, during an operation or a biopsy. The tissue sample is aseptically cut into small pieces and cultured in a medium suitable for the culture of the particular sample tissue (e.g., DMEM, Eagle, RPMI, (Gibco Co. Ltd.), soft agar or collagen matrix), according to standard methods of tissue culture (See, Nakai et al. (eds.) TISSUE CULTURE (1976)).

Any tissue which is a target for a hormone (e.g., it contains a hormone receptor and is capable of responding to the hormone by modulating its growth) may be useful for practicing the present invention. Preferred tissues for use in practicing the present invention include, but are not limited to, tumors found in mammary, endometrial, ovarian, and prostate cancers. Preferred cancer tissues for determining estrogen-dependent growth and/or the presence of aromatase activity are mammary, endometrial and ovarian cancers. A preferred cancer tissue for determining androgen-dependent growth and/or the presence of 5α-reductase activity is prostate cancer. Heretofore, only the presence of hormone receptors in these cancers has been widely investigated.

Any hormone synthetase substrate and inhibitor combination may be used in practicing the present invention, provided they are capable of stimulating cell growth and inhibiting it, respectively. A preferred hormone synthetase substrate of the present invention is the androgen testosterone, a substrate for aromatase. Accordingly, a preferred hormone synthetase inhibitor of the present invention is an aromatase inhibitor for example, 4-hydroxy-4-androsten-3,17-dione (generic name: formestane, Ciba-Geigy), 4-(5,6,7,8-tetrahydroimidazol[1,5a]pyridin-5-yl) benzonitrile monohydrochloride (generic name: fadorazole, Ciba Geigy); 14α-hydroxy-4-androsten-3,6,17-trione (code name: NKSO1, Snow Brand Milk Products, Co., Ltd.), shown in Japanese Laid-open (KOKAI) Patent Application No. 192794 (1988), 4-(5,6,7,8-tetrahydroimidazo-[1,5-α]-pyridin-5-yl)benzonitrile monohydrochloride hemihydrate (generic name: CGS16949A, product name: Afema, Novartis Co., Ltd).

Testosterone is also the substrate for the hormone synthetase 5α-reductase, by which it is converted to the androgen dihydrotestosterone. A preferred inhibitor of 5α-reductase is 17β-N,N-diethylcarbamoyl-4-aza-5α-androstan-3-one (generic name: 4MA, Merck Co., Ltd).

The above inhibitors are hereinafter referred to by their generic names.

Tissue proliferation can be determined by any art known method such as, for example, incorporation by the cells of a radiolabelled amino acid. Generally, measurement of $^3$H-hymldine uptake is chosen for its simplicity and convenience. To obtain an estimate of tissue growth $^3$H-thymidine is added to the culture media where appropriate, 3–4 days prior to the end of the treatment period, and is measured at the end of the culture period using liquid scintillation counting. The dpm emitted by the $^3$H-thymidine is divided by the DNA content in the tissue as an internal control for differences between the tissues in each treatment medium. The growth rate is calculated from the rate of growth in the control medium relative to the rates of growth in the medium containing a hormone synthetase substrate, or in the medium containing the hormone synthetase substrate and a synthetase inhibitor. The growth rate is estimated by the following equation: Growth rate (%)=100×[(the amount of incorporated $^3$H-thymidine in the respective additive-containing medium/the concentration of DNA in the tissue)/ (the amount of incorporated $^3$H-thymidine in the additive-free medium/the concentration of DNA in the tissue)].

The present invention further provides a new method for classifying the tissue lesions of patients with certain estrogen-dependent cancers, for example, mammary, endometrial or ovarian cancers. For example, if the growth of a cancer is estrogen-dependent and the cancer tissue contains the estrogen synthetase, aromatase, which converts testosterone to estrogen, then the tissue will grow in a medium with added testosterone. The promoted growth is suppressed by an aromatase inhibitor such as, for example, formestane, fadorazole, NKSO1 and CGS16949A. Thus, the excised tissue would be classified as a Type 1 hormone-dependent tumor (see Table 1 above). If the cancer tissue lacks estrogen-dependent growth and aromatase, then no stimulation of growth rate will be observed in the presence of testosterone and it would be classified as a Type 4 tumor.

The present invention also provides a new method for classifying the tissue lesions of patients with androgen-dependent cancers. For example, if the growth of a prostate cancer tumor is androgen-dependent and contains the dihydrotestosterone synthetase, 5α-reductase, which converts testosterone to dihydrotestosterone, then the tissue will grow in a medium with added testosterone. The promoted growth is suppressed by an 5α-reductase inhibitor, such as 4MA. Thus the excised tissue would be classified as a Type 1 hormone-dependent tumor (see Table 1 above). If the prostate cancer tissue lacks androgen-dependent growth and 5α-reductase, then no stimulation of growth rate will be observed in the presence of testosterone and it would be classified as a Type 4 tumor.

It is an important object of the invention to provide a method for the easy and simultaneous diagnosis of the presence or absence of a hormone synthetase and hormone-dependent proliferation in hormone-dependent tissues, such as tumors. It is contemplated that the present invention will provide new guidelines for the classification of tumors and the selection of medical treatment for patients, in particular cancer patients. For example, a Type 1 tumor of Table 1 is presumed to be treatable with a hormone synthetase inhibitor but Types 2, 3 or 4 would not. The present invention therefore provides a suitable medical treatment course for patients with these types of tumors.

In the method of the invention, testosterone is generally added to culture medium to a concentration of about 1–1,000 nM, preferably about 1–100 nM. The concentration of aromatase inhibitor used in the present invention depends upon its inhibitory activity and toxicity and is generally about 0.01–100 μM for NKSO1, CGS16949A or 4MA. The concentration of hormone synthetase inhibitor used in practicing the present invention must be non-toxic to the sample tissue and to the patient, if it is to be subsequently used as a treatment.

Practice of the invention will be still more fully understood from the following examples, which are presented herein below for illustration only and should not be considered as limiting the invention in any way.

EXAMPLE 1

The effects of hormone synthetase substrate and hormone synthetase inhibitor in mammary cancer tissue Biopsies from 21 patients with mammary cancer were obtained and a tissue section of 10×10 mm was excised from the center of each mammary tumor. The necrotic portion was removed and transferred aseptically to Hanks' solution (Gibco Co., Ltd.) containing 100 U/ml each of penicillin and streptomycin (Gibco Co., Ltd.), and the tissue was then cut into pieces of 0.5–1×0.5–1 mm with a scalpel. Four to five pieces of tissue were placed on collagen matrices in a 24-well microtiter plate. The collagen matrices were prepared as follows: Spongy collagen matrix (Spongostan Co., Ltd.) was aseptically cut into pieces of 1 $cm^3$, each placed into a well of a 24 well microtiter plate, and covered with phenol red-free modified Eagle MEM (Gibco Co., Ltd.) containing 10% fetal calf serum (FCS, Gibco Co., Ltd.) and 100 U/ml each of penicillin and streptomycin.

The prepared 24 well microtiter plate was placed in an atmosphere of 5% $CO_2$ and cultured at 37° C. for seven days. The culture medium was prepared using FCS treated with charcoal dextran and replaced every other day to keep the medium steroid-free.

Mammary cancer cells were given one of the following treatments: (1) the control group was grown in culture medium only, (2) the substrate group was grown in a medium with 10 nM testosterone added, and (3) the substrate and enzyme inhibitor group was grown in medium with 10 nM testosterone and 1 µM NKSO1 added. After seven days of culture, the culture media was changed to a media containing 0.67 µCi of $^3$H-thymidine and the cells were cultured for another three days. After culturing for three days, tissue tips on the collagen sponge in each well were transferred into tubes containing 1 ml of Hanks' solution containing 0.1 mg/ml of collagenase and incubated at 37° C. for a further eight hours. The cell mass was dispersed by pipetting and then centrifuged at 3,000 rpm for 10 minutes. The precipitates formed were mixed with 1 ml of 100 mM Tris buffer, pH 7.5, containing 1% sodium dodecylsulfate and 200 µg/ml of proteinase and incubated further at 50° C. for three hours. The resultant solution was mixed with 1 ml of a mixture of phenol/chloroform/isoamyl alcohol (25:24:1) for a few minutes. The mixture was centrifuged at 3,000 rpm for 10 minutes and the upper aqueous layer was removed and mixed with 100 µl of 3M sodium acetate and 2.5 ml of cold ethyl alcohol. Precipitated DNA was gathered round a glass rod and soaked in 70%, 80% and 90% aqueous ethyl alcohol, successively, and air dried. The dried DNA was resuspended in 1 ml of 100 mM Tris buffer, pH 7.5.

The concentration of DNA in the solution was determined by the Absorbance at 260 nm and the $^3$H-thymidine content of the solution was measured by liquid scintillation counting and expressed as dpm/µg DNA. The method of determining cell growth by $^3$H-thymidine incorporated per weight of DNA is widely used and can be performed by conventional methods such as those described by Fukuoka et al. 43, ACTA OBST. GYNAEC. JPN, 1667, (1973). The results are shown in Table 2. A tumor was deemed "antitumor effect positive" when there was a statistical significance in the volume of the tumor in the control group compared to that in the aromatase inhibitor treated group. There are several methods available for measuring the statistical significance of the effects and a T-test with a significance level of 5% or less was chosen.

TABLE 2

| Patient | Growth Rate (%) Medium with Testosterone | Medium with Inhibitor (NKSO1) | Diagnosis |
|---|---|---|---|
| A | 114.4 | 104.1 | |
| B | 96.9 | 95.0 | |

TABLE 2-continued

| Patient | Growth Rate (%) Medium with Testosterone | Medium with Inhibitor (NKSO1) | Diagnosis |
|---|---|---|---|
| C | 167.1 | 114.8 | |
| D | 100.7 | 97.7 | |
| E | 102.3 | 98.1 | |
| F | 114.6 | 98.6 | Type 1 |
| G | 104.0 | 107.4 | |
| H | 117.5 | 126.8 | |
| I | 120.5 | 99.8 | Type 1 |
| J | 101.2 | 117.7 | |
| K | 88.4 | 97.9 | |
| L | 120.9 | 97.2 | Type 1 |
| M | 129.7 | 77.4 | Type 1 |
| N | 100.3 | 95.2 | |
| O | 97.4 | 98.4 | |
| P | 156.4 | 101.3 | Type 1 |
| Q | 92.9 | 98.8 | |
| R | 108.8 | 95.2 | |
| S | 160.7 | 103.3 | Type 1 |
| T | 98.9 | 92.4 | |
| U | 92.6 | 93.6 | |

Mammary cancer tissues exhibiting estrogen-dependent proliferation and having aromatase activity were found in six out of 21 patients by the examination method of the present invention. The proliferation of these mammary cancer cells was hormone-dependent and was presumed to be regulated by hormones synthesized in their tumor tissues.

EXAMPLE 2

The effects of hormone synthetase substrate and hormone synthetase inhibitor on cell lines in vitro and tumor tissue derived from those cell lines in vivo The effectiveness of using an aromatase inhibitor to inhibit cell proliferation according to the present invention was examined using four tumor cell lines of human origin (Table 3). These cell lines were examined for the expression of estrogen receptor according to standard methods well known in the art and the results are summarized in Table 3.

TABLE 3

| Tumor Cell line | Tissue Source | Presence of Estrogen Receptor |
|---|---|---|
| MCF-7 | Human mammary cancer | Yes |
| BG-1 | Human ovarian cancer | Yes |
| R-27 | Human mammary cancer | Yes |
| ISHIKAWA | Human endometrial cancer | Yes |

Each of the above cell lines was inoculated subcutaneously into the axillary fossa of 7-week-old female nude mice at $1×10^5$ cells/0.1 ml/mouse to give solid tumors. The tumors were grown to approximately 1 cm diameter and resected and cultured according to the procedure described in Example 1. The cultured tumor cells were given one of the following treatments: (1) the control group was grown in medium only, (2) the substrate group was grown in medium with 10 nM testosterone added, and (3) the substrate and enzyme inhibitor group was grown in medium with 10 nM testosterone and 1 µM NKSO1 added. The cells were cultured and cell growth measured as described in Example 1. The results are shown in Table 4. A tumor was deemed "Type 1" according to the statistical method described in Example 1.

TABLE 4

| Tumor Cell line | Growth rate (%) | | Diagnosis |
|---|---|---|---|
| | Testosterone | Inhibitor (NKSO1) | |
| MCF-7 | 635.3 | 102.0 | Type 1 |
| BG-1 | 288.7 | 117.6 | Type 1 |
| R-27 | 106.7 | 102.9 | Type 2 |
| ISHIKAWA | 307.0 | 279.2 | Type 2 |

These tumor-derived cell lines were re-inoculated subcutaneously into the axillary fossa of 7-week-old female nude mice at $1 \times 10^5$ cells/0.1 ml/mouse to form solid tumors. The mice were divided into two groups each containing 10 mice and treated as follows until the tumor mass became approximately 3 mm in diameter: (1) a control group, to which an aromatase inhibitor was not administered, and (b) a test group to which an aromatase inhibitor was administered every day until the test was over.

The aromatase inhibitors administered included NKSO1, formestane, and fadorazole. NKSO1 was administered orally at a dosage of 100 mg/kg/day and formestane was administered subcutaneously at a dosage of 50 mg/kg/day. Fadorazole was administered orally at a dosage of 25 mg/kg/day for MCF-7 tumor injected mice, 60 mg/kg/day for BG-1 tumor injected mice, and 3 mg/kg/day for R-27 tumor injected mice. The administration period of the inhibitors depended upon the proliferation rates of the respective tumors in the nude mice, and was 28 days for BG-1, R-27 and ISHIKAWA, and 42 days for MCF-7. The longer and shorter axes of the tumors were determined on the next day after the final administration using a vernier caliper. The volume of the tumors was calculated using the following equation: Estimated volume of tumor=(longer axis)×(shorter axis)$^2$×0.5.

The antitumor effects of the aromatase inhibitors on mice injected with the tumor cells derived from the four tumor cell lines are shown in Table 5.

TABLE 5

| Tumor Cell line | Control Group | Aromatase Inhibitor | | |
|---|---|---|---|---|
| | | NKSO1 | Formestane | Fadorazole |
| MCF-7 | 635 ± 89[1] | 339 ± 46 (p < 0.05)[2] Effective | 289 ± 68 (p < .05) Effective | 255 ± 41 (p < 0.05) Effective |
| BG-1 | 1,022 ± 309 | 394 ± 78 (p < 0.05) Effective | ND | 401 ± 86 (p < 0.05) Effective |
| R-27 | 1,298 ± 266 | 1,145 ± 245 Not Effective | ND | 1,321 ± 564 Not effective |
| ISHIKAWA | 1,357 ± 576 | 1,435 ± 746 Not Effective | ND | ND |

1): Estimated volume of tumor [Average ± SD (mm$^3$)]
2): T-test result with those of the control group.
ND: No experiment was performed.

The results obtained in the treatment of the tumor derived-cells with the aromatase inhibitor using the method of the present invention correlated with the practical therapeutic effect of aromatase inhibitor treatment as shown in Table 6 below. As shown by the above mentioned examples, the examination method of the present invention clearly distinguished the indications of aromatase inhibitor therapy for mice with an estrogen dependent tumor.

TABLE 6

| Tumor Cell Line | Indication for aromatase inihibitor therapy | Tumor Type | Aromatase Inhibitor | | |
|---|---|---|---|---|---|
| | | | NKSO1 | Formestane | Fadorazole |
| MCF-7 | Indicated | 1 | Effective | Effective | Effective |
| BG-1 | Indicated | 1 | Effective | ND | Effective |
| R-27 | Not inicated | 2 | Not Effective | ND | Not Effective |
| ISHI-KAWA | Not indicated | 2 | Not Effective | ND | ND |

ND: No experiment was performed

EXAMPLE 3

The effects of a hormone synthetase substrate and hormone synthetase inhibitor on endometrial cancer tissue Biopsies from 15 patients with endometrial cancer were obtained and cultured according to Example 1. The cultured endometrial cancer cells were given one of the following treatments: (1) the control group was grown in medium only, (2) the substrate group was grown in a medium with 10 nM testosterone added, or (3) the substrate and enzyme inhibitor group was grown in a medium with 10 nM testosterone, 1 μM NKSO1 and 10 nM CGS16949A added. The cells were cultured and cell growth measured as described in Example 1. The results are shown in Table 7. A tumor was deemed "Type 1" according to the statistical method described in Example 1.

TABLE 7

| Patient | Growth Rate (%) | | Diagnosis |
|---|---|---|---|
| | Testosterone | Inhibitor[a,b] | |
| A | 102.3% | 102.8%[a] | |
| B | 143.6% | 105.7%[a] | TYPE 1 |
| C | 102.1% | 98.9%[a] | |
| D | 110.8% | 105.8%[a] | |
| E | 106.0% | 100.4%[a] | |
| F | 156.5% | 108.6%[a] | TYPE 1 |
| G | 104.4% | 105.3%[a] | |
| H | 109.2% | 100.9%[a] | |
| I | 107.8% | 104.4%[a] | |
| J | 105.5% | 99.1%[a] 98.2%[b] | |
| K | 107.9% | 109.6%[a] 108.9%[b] | |
| L | 145.1% | 108.1%[a] 109.7%[b] | TYPE 1 |
| M | 187.7% | 110.5%[a] 109.9%[b] | TYPE 1 |
| N | 101.1% | 106.4%[a] 105.5%[b] | |
| O | 103.6% | 104.0%[a] 103.6%[b] | |

[a] NKSO1
[b] CGS16949A

As shown in Table 7, four of the fifteen cancers were determined to be Type 1 tumors.

EXAMPLE 5

The effects of hormone synthetase substrate and hormone synthetase inhibitor on ovarian cancer tissue Biopsies from 9 patients with ovarian cancer were obtained and cultured according to Example 1. The cultured ovarian cancer cells were given one of the following treatments: (1) the control group was grown in medium only, (2)

the substrate group was grown in a medium with 10 nM testosterone added, or (3) the substrate and enzyme inhibitor group was grown in a medium with 10 nM testosterone, 1 μM NKSO1 and 10 nM CGS16949A added. The cells were cultured and cell growth measured as described in Example 1. The results are shown in Table 8. A tumor was deemed "Type 1" according to the statistical method described in Example 1.

TABLE 8

| | Growth Rate (%) | | |
|---|---|---|---|
| Patient | Testosterone | Inhibitor[a,b] | Diagnosis |
| A | 141.2% | | 105.2%[a] | TYPE 1 |
| B | 133.0% | | 102.1%[a] | TYPE 1 |
| C | 101.8% | | 94.6%[a] | |
| D | 103.4% | | 100.7%[a] | |
| E | 142.9% | | 106.5%[a] | TYPE 1 |
| F | 102.1% | 103.3%[a] | 99.1%[a] | |
| G | 107.1% | 101.2%[a] | 99.5%[a] | |
| H | 103.7% | 97.1%[a] | 102.7%[a] | |
| I | 144.2% | 105.5%[a] | 110.3%[a] | TYPE 1 |

[a] NKSO1
[b] CGS16949A

As shown in Table 8, four of the nine cancers were determined to be Type 1 tumors.

EXAMPLE 6

The effects of hormone synthetase substrate and hormone synthetase inhibitor on prostate cancer tissue Biopsies from 8 patients with prostate cancer were obtained and cultured according to Example 1. The cultured prostate cancer cells were given one of the following treatments: (1) the control group was grown in medium only, (2) the substrate group was grown in medium with 10 nM testosterone added, and (3) the substrate and enzyme inhibitor group was grown in a medium with 10 nM testosterone and 1 μM 4MA added. The cells were cultured and cell growth measured as described in Example 1. The results are shown in Table 9. A tumor was deemed "Type 1" according to the statistical method described in Example 1.

TABLE 9

| | Growth rate (%) | | |
|---|---|---|---|
| Patient | Testosterone | Inhibitor (4MA) | Diagnosis |
| A | 101.1% | 97.8% | |
| B | 173.1% | 107.0% | TYPE 1 |
| C | 167.2% | 105.6% | TYPE 1 |
| D | 111.6% | 104.4% | |
| E | 191.2% | 112.5% | TYPE 1 |
| F | 161.0% | 102.8% | TYPE 1 |
| G | 104.1% | 102.2% | |
| H | 172.5% | 107.9% | TYPE 1 |

As shown in Table 9, five of the nine cancers were determined to be Type 1 tumors.

Equivalents

Those skilled in the art will be able to ascertain many equivalents to the specific embodiments described herein. Such equivalents are intended to be encompassed by the scope of the following claims.

What is claimed is:

1. A method for predicting the effectiveness of a hormone synthetase inhibitor therapy for treating a patient who has a tumor which may be hormone dependent comprising:

(a) culturing a sample of a tumorous tissue taken from the patient in (i) a control medium, (ii) said control medium further comprising a substrate for a hormone synthetase, and (iii) said control medium further comprising a substrate for a hormone synthetase and an inhibitor of said hormone synthetase;

(b) measuring the growth of said tumorous tissue in media (i), (ii) and (iii);

(c) comparing the growth rates of said tumorous tissue in media (ii) relative to (i) and in media (iii) relative to media (i);

(d) determining simultaneously therefrom the presence or absence of hormone-dependent growth of said tissue and the presence or absence of a hormone synthetase in said tissue; and (e) treating the patient with a hormone synthetase inhibitor if said tissue is determined to be hormone-dependent and to possess a hormone synthetase.

2. The method of claim 1 wherein said tumorous tissue is selected from the group consisting of mammary tumor tissue, endometrial tumor tissue, ovarian tumor tissue and prostate tumor tissue.

3. The method of claim 1 wherein said hormone is estrogen.

4. The method of claim 1 wherein said hormone is dihydrotestosterone.

5. The method of claim 1 wherein said hormone synthetase substrate is testosterone.

6. The method of claim 1 wherein said hormone synthetase is aromatase.

7. The method of claim 1 wherein said hormone synthetase is 5α-reductase.

8. The method according to claim 1 wherein said hormone synthetase inhibitor is selected from the group consisting of 4-hydroxy-4-androsten-3,17-dione, 4-4(5,6,7,8-tetrahydroimidazol[1,5a]pyridin-5-yl)benzonitrile monohydrochloride, 14α-hydroxy-4-androsten-3,6,17-trione, 4-(5,6,7,8-tetrahydroimidazol-[1,5-α]-pyridin-5-yl) benzonitrile monohydrochloride hemihydrate and 17β-N,N-diethylcarbamoyl-4-aza-5αandrostan-3-one.

* * * * *